(12) United States Patent
Smith (10) Patent No.: US 7,179,616 B1
(45) Date of Patent: Feb. 20, 2007

(54) METHOD FOR DETECTING PHOSPHATIDYLSERINE ON THE SURFACE OF CELLS

(75) Inventor: Bradley D. Smith, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 427 days.

(21) Appl. No.: 10/656,237

(22) Filed: Sep. 8, 2003

Related U.S. Application Data (60) Provisional application No. 60/416,233, filed on Oct. 7, 2002.

(51) Int. Cl.
*G01N 1/30* (2006.01)
*G01N 21/76* (2006.01)
*G01N 33/533* (2006.01)

(52) U.S. Cl. .................. 435/40.5; 436/86; 436/87; 436/172; 436/501; 436/800

(58) Field of Classification Search ............... 435/40.5; 436/501, 87, 86, 172, 800
See application file for complete search history.

(56) References Cited

U.S. PATENT DOCUMENTS 5,834,196 A    11/1998   Reutelingsperger

OTHER PUBLICATIONS

Boon et al, "Chemical Control of Phospholipid Distribution Across Bilayer Membranes," *Medicinal Research Reviews*, 2002, vol. 22, No. 3, 251-281.
Daleke et al, "Identification and purification of aminophospholipid flippases," *Biochimica et Biophysica Acta*, 2000, No. 1486, 108-127.
Laakko et al, "Versatility of merocyanine 540 for the flow cytometric detection of apoptosis in human and murine cells," *Journal of Immunological Methods*, 2002, No. 261, 129-139.
Zweifach, "FM1-43 reports plasma membrane phospholipid scrambling in T-lymphocytes," *Biochem. J.*, 2000, No. 349, 255-260.
Balasubramanian et al, "Binding of Annexin V to Membrane Products of Lipid Peroxidation," *Biochemistry*, 2001, vol. 40, No. 30, 8672-8676.
Kamp et al, "Inhibition and Stimulation of Phospholipid Scrambling Activity. Consquences for Lipid Asymmetry, Echinocytosis, and Microvesiculation of Erythrocytes," *Biochemistry*, 2001, vol. 40, No. 31, 9438-9446.
Meers et al, "Calcium-Dependent Annexin V Binding to Phospholipids: Stoichiometry, Specificity, and the Role of Negative Charge," *Biochemistry*, 1993, vol. 32, No. 43, 11711-11721.
Van Engeland et al, "Annexin V-Affinity Assay: A Review on an Apoptosis Detection System Based on Phosphatidylserine Exposure," *Cytometry*, 1998, vol. 31, 1-9.

Williamson et al, "Phosphatidylserine Exposure and Phagocytosis of Apoptotic Cells," *Methods in Cell Biology*, 2001, vol. 66, Chapter 15, 339-364.
Van Heerde et al, "Markers of apoptosis in cardiovascular tissues: focus on Annexin V," *Cardiovascular Research*, 2000, vol. 45, 549-559.
Schlegel et al, "Phosphatidylserine, a death knell," *Cell Death and Differentiation*, 2001, vol. 8, 551-563.
Hengartner, "The biochemistry of apoptosis," *Nature*, Oct. 2000, vol. 407, 770-776.
Ojida et al, "First Artificial Receptors and Chemosensors toward Phosphorylated Peptide in Aqueous Solution," *J. Am. Chem. Soc.*, May 2002, vol. 124, No. 22, 6256-6258.
Ojida et al., "Efficient fluorescent ATP-sensing based on coordination chemistry under aqueous neutral conditions," *Tetrahedron Letters*, 2002, vol. 43, 6193-6195.
Meers et al, "Interactions of Annexins with Membrane Phospholipids," *Biochemistry*, 1991, vol. 30, No. 11, 2903-2908.
Kimura et al, "A macrocyclic zinc(II) fluorophore as a detector of apoptosis," *PNAS*, Apr. 2003, vol. 100, No. 7, 3731-3736.
Pläsier et al, "Automatic image analysis for quantification of apoptosis in animal cell culture by annexin-V affinity assay," *Journal of Immunological Methods*, 1999, vol. 229, 81-95.
Ojida, et al. "Molecular Recognition and Fluorescence Sensing of Monophosphorylated Peptides in Aqueous Solution by Bls(zinc(II)—dipicolytamine)-Based Artificial Receptors" Journal of American Chemical Society, 126 (Feb. 2004). p. 2454-2463.
Koulov, et al. "Biophysical Studies of a Synthetic Mimic of the Apoptosis-Detecting Protein Annexin V" Israel Journal of Chemistry, 45 (Jan. 2005), p. 373-379.

*Primary Examiner*—Mary E. Ceperley
(74) *Attorney, Agent, or Firm*—Michael G. Verga

(57) ABSTRACT

The present invention relates generally to a method and compound for sensing the presence of anionic phospholipids, especially phosphatidylserine, on the surface of vesicles and cells. Upon introducing a compound having the structure below to a sample of cells or vesicles, the compound binds to anionic phopholipids on the surface of cells or vesicles and the presence of the compound is detected reflecting the presence of anionic phospholipids in the sample

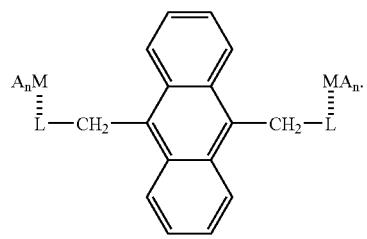

5 Claims, 8 Drawing Sheets

METHOD FOR DETECTING PHOSPHATIDYLSERINE ON THE SURFACE OF CELLS

CROSS-REFERENCE TO RELATED APPLICATIONS

This application makes reference to and claims priority to U.S. Provisional Patent Application No. 60/416,233, entitled "Method for Detecting Phosphatidylserine on the Surface of Cells," filed Oct. 7, 2002. The entire disclosure and contents of the above application is hereby incorporated by reference.

BACKGROUND OF THE INVENTION

1. Field of the Invention

The present invention relates generally to a method and compound for sensing the presence of anionic phospholipids, especially phosphatidylserine, on the surface of vesicles and cells.

2. Description of the Prior Art

The asymmetric transmembrane distribution of phospholipids is a fundamental feature of normal cell operation. In the case of animal plasma membranes, most of the phosphatidylethanolamine (PE) and phosphatidylserine (PS) is sequestered in the inner monolayer of the membrane; whereas, most of the phosphatidylcholine (PC) and sphingomyelin (SM) is in the membrane outer monolayer, see Boon, J. M. & Smith, B. D. (2002) Med. Res. Rev., 22, 251–81, the entire contents and disclosure of which is hereby incorporated by reference. This organization of lipids is generated and maintained by the concerted action of a number of phospholipid translocases that vary in lipid specificity, energy requirements, and direction of translocation, see Daleke, D. L. & Lyles, J. V. (2000) Biochim. Biophys. Acta, 1486, 108–27, the entire contents and disclosure of which is hereby incorporated by reference. The appearance of PS on the cell surface is one of the hallmarks of the early/intermediate stages of cell apoptosis and is believed to occur prior to DNA fragmentation, morphological changes, and plasma membrane permeabilization, see Schlegel, R. A. & Williamson, P. (2001) Cell Death Differ., 8, 551–63; van Heerde, W. L., Robert-Offerman, S., Dumont, E., Hofstra, L., Doevendans, P. A., Smits, J. F., Daemen, M. J. & Reutelingsperger, C. P. (2000) Cardiovasc. Res., 45, 549–59; and Williamson, P., van den Eijnde, S. & Schlegel, R. A. (2001) Meth. Cell Biol., 66, 339–64, the entire contents and disclosures of which are hereby incorporated by reference. The clearest assessment of cell apoptosis is gained from microscopy or flow cytometry analyses that examine large cell populations and identify and quantify sub-populations. A common method of detecting PS on a cell surface is to use the PS-binding protein annexin V, see van Heerde, W. L., Robert-Offerman, S., Dumont, E., Hofstra, L., Doevendans, P. A., Smits, J. F., Daemen, M. J. & Reutelingsperger, C. P. (2000) Cardiovasc. Res., 45, 549–59; Williamson, P., van den Eijnde, S. & Schlegel, R. A. (2001) Meth. Cell Biol., 66, 339–64; van Engeland, M., Nieland, L. J., Ramaekers, F. C., Schutte, B. & Reutelingsperger, C. P. (1998) Cytometry, 31, 1–9, the entire contents and disclosures of which are hereby incorporated by reference. In the presence of sufficient calcium, this 35 Kd protein has a strong affinity for membranes that are rich in negatively charged phospholipids, see Meers, P. & Mealy, T (1993) Biochemistry, 32:11711, the entire contents and disclosures of which are hereby incorporated by reference. In particular, the association constant for annexin V binding to membranes that are rich in PS is around $10^8$ $M^{-1}$, see Meers P. et al. (1991) Biochemistry, 30:2903, the entire contents and disclosure of which is hereby incorporated by reference. The utility of annexin V is derived from its selective affinity for cell plasma membranes that have externalized phosphatidylserine (PS), see van Engeland, M., Nieland, L. J., Ramaekers, F. C., Schutte, B. & Reutelingsperger, C. P. (1998) Cytometry, 31, 1–9, the entire contents and disclosure of which is hereby incorporated by reference. Annexin V is labeled with a probe, typically a fluorescent dye such as fluorescein, to allow detection by flow cytometry or an imaging method such as fluorescence microscopy. Although annexin V is a useful reagent, it is a protein with some technical drawbacks. It is susceptible to degradation and thus requires careful storage. Another concern is that up to 2.5 mM of extracellular $Ca^{2+}$ may be needed for complete membrane binding, see Williamson, P., van den Eijnde, S. & Schlegel, R. A. (2001) Meth. Cell Biol., 66, 339–64, the entire contents and disclosure of which is hereby incorporated by reference. This may lead to false positive results because most animal cells have a $Ca^{2+}$ dependent scramblase that may move PS to the cell surface (concentration for half maximal activation of the scramblase is 25–100 μM), see Kamp, D., Sieberg, T. & Haest, C. W. (2001) Biochemistry, 40, 9438–46, the entire contents and disclosure of which is hereby incorporated by reference. In addition, annexin V is known to associate with membrane surfaces that contain the byproducts of lipid peroxidation, see Balasubramanian, K., Bevers, E. M., Williams, G. M. & Schroit, A. J. (2001) Biochemistry, 40, 8672–8676, the entire contents and disclosure of which is hereby incorporated by reference. Furthermore, complete annexin V binding requires incubation times of up to one hour, which is problematic for kinetic assays, Zweifach, A. (2000) Biochem. J., 349, 255–60, and Williamson, P., van den Eijnde, S. & Schlegel, R. A. (2001) Meth. Cell Biol., 66, 339–64, the entire contents and disclosures of which are hereby incorporated by reference. In summary, dye labeled annexin V is used extensively as a PS-sensing reagent, but there is a need for a more stable, low-molecular-weight mimic that can sense PS-rich membranes rapidly and independently of $Ca^{2+}$ levels.

The idea that a small molecule, instead of a large protein such as annexin V, may be used to detect membrane changes, such as those due to cell apoptosis, is supported by work with the fluorescent dyes MC540 and FM1-43, Laakko, T., King, L. & Fraker, P. (2002) J. Immunol. Meth., 261, 129–39, and Zweifach, A. (2000) Biochem. J., 349, 255–60, the entire contents and disclosures of which are hereby incorporated by reference. The binding of MC540 to membranes is sensitive to membrane composition and increases with apoptotic cells, see Williamson, P., van den Eijnde, S. & Schlegel, R. A. (2001) Meth. Cell Biol., 66, 339–64, the entire contents and disclosures of which are hereby incorporated by reference. However, there are disadvantages with MC540. The signal difference between normal cells and apoptotic cells is only about five fold (it is up to 100-fold with annexin V); furthermore, the dye is phototoxic. Likewise, FM1-43 is a cationic dye that binds more tightly to membranes that are rich in anionic phospholipids and gives a signal difference between normal and apoptotic cells of 6–10 fold. A problem with FM1-43 is its broad emission (515–595 nm), which makes it difficult to use a second fluorophore that emits in the fluorescein or rhodamine channels.

SUMMARY OF THE INVENTION

It is therefore an object of the present invention to provide a low-molecular-weight fluorescent chemical that can sense PS-rich membranes rapidly and independently of $Ca^{2+}$ levels.

It is a further object to provide a fluorescent PS-binding compound that can be used to identify dead and apoptotic cells using fluorescence microscopy.

It is yet another object to provide a fluorescent PS-binding compound that can be used to identify dead and apoptotic cells using flow cytometry.

It is yet another object to provide a fluorescent PS-binding compound that can be used to identify dead and apoptotic cells using bulk solution, fluorescence spectroscopy.

In all of the above embodiments, it is an object to provide a high-throughput assay for necrotic or apoptotic cell death that can be used in drug discovery or biotechnology processes.

In all of the above embodiments, it is an object to provide a fluorescent sensing compound that can quantify the amount of anionic phospholipids on a cell or vesicle surface.

In a first broad aspect of the present invention, there is provided a method for determining the presence of anionic phospholipids in a sample of cells or vesicles, comprising introducing a compound having the following structure to the sample wherein the compound binds to the anionic phopholipids on the surface of the cells or vesicles; and detecting the presence of the compound via its fluorescence emission which indicates the presence of anionic phospholipids in the sample upon association of the compound with the anionic phospholipids.

In a second broad aspect of the present invention, there is provided a method for determining the presence of anionic phospholipids in a sample of cells or vesicles, comprising introducing a compound having the following structure to the sample wherein the compound binds to the anionic phopholipids on the surface of the cells or vesicles; and detecting the presence of the compound via its fluorescence emission which indicates the presence of anionic phospholipids in the sample upon association of the compound with the anionic phospholipids, wherein said compound further comprises at least two ligands at positions selected from the group consisting of 1,2; 1,3; 1,4; 1,5; 1,6; 1,7; 1,8; 1,9; 1,10; 2,3; 2,4; 2,5; 2,6; 2,7; 2,8; 2,9; and 2,10, wherein said ligands comprise wherein M is a divalent or trivalent transition or lanthanide metal cation, A is a weakly coordinating counter anion, and L is a metal cation binding ligand.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "anionic phospholipids" refers to phospholipids with anionic head groups, such as phosphatidylserine, phosphatidic acid, phosphatidylglycerol, phosphatidylinositol, etc.

For the purposes of the present invention, the term "dead cell" refers to a necrotic or late apoptotic cell that may be suspended in solution, adhered to a surface, or part of a heterogeneous tissue. The cell plasma membrane is sufficiently permeable to allow staining by DNA binding dyes such as trypan blue, propidium iodide (PI) or 7-aminoactinomycin D (7AAD).

For the purposes of the present invention, the term "apoptotic cell" refers to a cell that may be suspended in solution, adhered to a surface, or part of a heterogeneous tissue. The cell plasma membrane is sufficiently impermeable to not allow staining by DNA binding dyes such as trypan blue, propidium iodide (PI) or 7-aminoactinomycin D (7AAD).

For the purposes of the present invention, the term "low calcium environment" refers to an environment in which calcium is in a concentration of approximately 2 mM or less.

For the purposes of the present invention, the term "substantially calcium free environment" refers to an environment having no more than trace amounts of calcium.

For the purposes of the present invention, the term "calcium independent" refers to a compound that is not dependent on or does not require the presence of calcium to effect membrane binding or association.

For the purposes of the present invention, the term "metal cation M" refers to a divalent or trivalent metal cation. A metal cation M may be a member of the transition metals such as $Zn^{2+}$, $Cu^{2+}$, $Ni^{2+}$, $Co^{3+}$, etc., or the lanthanide series such as $Eu^{3+}$, $Nb^{3+}$, etc.

For the purposes of the present invention, the term "metal cation binding ligand L" refers to a chemical group or sub-structure that can form strong coordination bonds to a metal cation.

For the purposes of the present invention, the term "weakly coordinating anion A" refers to a suitable counter anion for a metal cation that does not prevent the metal cation from interacting with the anionic residues on the phospholipid head group. The anion may or may not dissociate from the metal cation when in aqueous solution. Examples of such anions include but are not limited to $Cl^-$, $Br^-$, $I^-$, $CH_3COO^-$, $HPO_3^-$, $HSO_4^-$, $SO_4^{2-}$, $NO_3^-$, etc.

For the purposes of the present invention, the term "coordination complex" refers to a molecule composed of metal cations bonded to ligands which are in turn covalently attached to an anthracene core.

For the purposes of the present invention, the term "anthracene core" refers to a central anthracene unit that serves two roles. It is the molecular scaffold that is connected to the two or more metal cation binding ligands, and it is the part of the coordination complex that produces the fluorescence. The anthracene core may be further substituted with functional groups like nitro, halogen, sulfonyl or carbonyl, etc. that provide more favorable physical, supramolecular or photochemical properties.

DESCRIPTION

The present invention provides for a family of chemical compounds that are sensitive sensors for the cell membrane constituent phosphatidylserine (PS). This family of sensing compounds, referred to in the present application as phosphatidylserine sensors (PSS), detects the appearance of PS on the surface of cells. The level of PS on a cell surface provides important information about the state of the cell. In particular, a raised level of PS is the hallmark of the early/intermediate stages of cell apoptosis (programmed cell death). It is extremely useful to know if and when a cell is undergoing apoptosis. At present a dye-labeled protein called annexin V is used for this purpose, see U.S. Pat. No. 5,834,196, the entire contents and disclosure of which is hereby incorporated by reference. However, annexin V has certain technical problems such as its susceptibility to degradation, its requirement for high levels of extracellular $Ca^{2+}$, and its slow binding kinetics. In many imaging circumstances, PSS compounds may be used as a substitute for annexin V without the negative aspects of annexin V. The PSS compounds should be useful in various biomedical research and clinical situations that use the imaging techniques of fluorescence microscopy and/or flow cytometry, and drug discovery or biotechnology processes that require high-throughput assays for apoptosis.

Apoptosis is a programmed cell death mechanism that many organisms utilize to selectively eliminate cells which show either deleterious reactivities to the host or which have not received a full complement of activation or survival signals. Although comparable in their final outcome, necrosis and apoptosis are distinctly different processes. Fundamental differences between the two death-generating mechanisms are evident in the triggers necessary to initiate the two events. Necrosis is usually the result of an accumulation of toxic reagents within cells while apoptosis may be triggered by various environmental stimuli which lead to the activation of protease activity, see Hengartner, M. O. (2000) Nature, 407:770, the entire contents and disclosure of which is hereby incorporated by reference. At the cell membrane level, disruption of internal and external membranes is a normal consequence of necrosis. Alternatively, during programmed cell death, loss of cell membrane integrity is a very late event usually preceded by the destructive action of endogenous cellular enzymes, see van Engeland, M., Nieland, L. J., Ramaekers, F. C., Schutte, B. & Reutelingsperger, C. P. (1998) Cytometry, 31, 1–9, the entire contents and disclosure of which is hereby incorporated by reference.

The ability to exclude DNA binding dyes such as trypan blue, propidium iodide (PI) or 7-aminoactinomycin D (7AAD) is a property of cells that have an intact plasma membrane. Cells in the early phases of apoptosis fall into this category. On the other hand, late-stage apoptotic or necrotic cells have lost membrane integrity and therefore easily stain with DNA binding dyes.

The present invention describes the membrane binding and fluorescence sensing properties of a family of chemical compounds called phosphatidylserine sensors (PSS). The compounds are coordination complexes and are derivatives of anthracene. Attached to the core anthracene structure are two or more metal cation binding ligands, which form strong coordination bonds to two or more divalent or trivalent metal cations M such as $Zn^{2+}$, $Cu^{2+}$, $Ni^{2+}$, $Co^{2+}$, $Eu^{3+}$, $Nb^{3+}$, etc. To balance the charges, the compounds also include a weakly coordinating counter anion A such as $Cl^-$, $Br^-$, $I^-$, $CH_3COO^-$, $HPO_3^-$, $HSO_4^-$, $SO_4^{2-}$, $NO_3^-$, etc, wherein n indicates the stochiometry.

Shown above is a version of PSS with two metal cation binding ligands attached to the 9 and 10 positions of anthracene. Although this isomer will be the focus of the following discussions, it is noted that all other disubstituted isomers are included within the scope of the present invention; that is with metal cation binding ligands attached at the 1,2; 1,3; 1,4; 1,5; 1,6; 1,7; 1,8; 1,9; 1,10; 2,3; 2,4; 2,5; 2,6; 2,7; 2,8; 2,9 and 2,10 positions. Also within the scope of the present invention are versions of PSS with three or four metal cation binding ligands attached to the anthracene core.

The purpose of the metal cation binding ligand L is to form strong coordination bonds to the metal cation, but not all coordination sites of the metal cation are filled which allows the metal cation to simultaneously interact with the anionic residues on the PS head group. Preferred choices for the metal cation binding ligand are heteroaromatic containing compounds such as bis(2-pyridylmethyl)amine (DPA) and terpyridine (TPY), and polyamines such as tri(aminoethyl)amine (TREN), 1,4,7-triazacyclononane (TACN), 1,4,7,10-tetraazacyclododecane (TACD) and 1,4,8,11-tetraazacyclotetradecane (TACT), each shown below.

Thus, the present invention provides a method for determining the presence of anionic phospholipids in a sample of cells or vesicles, comprising introducing a compound having the following structure to the sample wherein the compound binds to the anionic phopholipids on the surface of the cells or vesicles; and detecting the presence of the compound via its fluorescence emission which indicates the presence of anionic phospholipids in the sample upon association of the compound with the anionic phospholipids, wherein A comprises a weakly coordinating counter anion and n indicates the stochiometry.

The present invention also provides a method for determining the presence of anionic phospholipids in a sample of cells or vesicles, comprising introducing a compound having the following structure to the sample wherein the compound binds to the anionic phopholipids on the surface of the cells or vesicles; and detecting the presence of the compound via its fluorescence emission which indicates the presence of anionic phospholipids in the sample upon association of the compound with the anionic phospholipids, wherein said compound further comprises at least two ligands at positions selected from the group consisting of 1,2; 1,3; 1,4; 1,5; 1,6; 1,7; 1,8; 1,9; 1,10; 2,3; 2,4; 2,5; 2,6; 2,7; 2,8; 2,9; and 2,10, wherein said ligands comprise wherein M is a divalent or trivalent transition or lanthanide metal cation, A is a weakly coordinating counter anion, and L is a metal cation binding ligand.

One specific compound in this family is called PSS-380, an anthracene derivative that is substituted in the 9 and 10 positions with two DPA ligands that each bind a zinc nitrate. PSS-380 was recently reported to bind phosphorylated compounds like phosphotyrosine in water with association constants around $10^7$ M$^{-1}$, see Ojida, A., Mito-Oka, Y., Inoue, M. A. & Hamachi, I. (2002) J. Am. Chem. Soc., 124, 6256–6258, the entire contents and disclosure of which is hereby incorporated by reference. The strong association is due to the dianionic tyrosine phosphate group coordinating simultaneously with the two zinc dications. Moreover, PSS-380 was shown to bind an anionic peptide sequence about one thousand times more strongly than a near-neutral sequence. PSS-380 does not bind to monoanionic phosphate diesters such as dimethyphosphate. Ojida, A., Park, S.; Mito-Oka, Y. & Hamachi, I. (2002) Tetrahedron Lett., 43, 6193–6195, the entire contents and disclosure of which is hereby incorporated by reference. However, as identified in the present invention, PSS-380 does associate with the head groups of monoanionic phospholipids when the phospholipids are part of a vesicle or cell membrane. Moreover, PSS-380 has no apparent affinity with membranes composed only of zwitterionic phospholipids. In the present invention, PSS-380 is shown to sense the presence of anionic phospholipids, especially PS, on the surface of vesicles and cells. In addition, the present invention demonstrates the ability of PSS-380 to act as a fluorescent sensor of apoptotic cells.

The fluorescence of PSS-380, is not affected if it is treated with monodispersed phospholipids of any charge, or vesicles composed of zwitterionic phosphatidylcholine. However, the fluorescence intensity increases up to ten-fold if PSS-380 interacts with vesicle membranes containing more than a few percent of the anionic phospholipids, phosphatidylserine, phosphatidylglycerol, or phosphatidic acid. The sensing effect is cooperative; not only does association increase if the vesicles have raised levels of anionic phospholipid but so does the maximum fluorescence at sensor saturation. The fluorescence emission of anthracene zinc dipicolylamine (AZD), shown below, a derivative of PSS-380, with one zinc dipicolylamine group, is hardly changed when it is treated with anionic vesicles, which suggests that the fluorescence enhancement with PSS-380 is not solely due to a membrane-induced change in polarity. Fluorescence microscopy and flow cytometry experiments with various cell lines indicate that PSS-380 can detect apoptotic and dead cells due to the appearance of phosphatidylserine on the cell surface.

PSS-380

AZD

Vesicle Studies with PSS-380

Unilamellar vesicles were prepared by initial hydration of a dried lipid film followed by repeated extrusion through polycarbonate membranes having a pore size of 100 nm. Aliquots of vesicle suspension were added to a solution of PSS-380 (1 μM, 3 mL) in HEPES buffer (10 mM) at pH 7.2. The fluorescence emission intensity at 440 nm (ex 380 nm) was measured 15 seconds after the addition of each aliquot. Control experiments showed that PSS-380 does not induce leakage of carboxyfluorescein from POPS:POPC (1:1) vesicles at low or high phospholipid to PSS-380 ratios, and does not promote the flip-flop of fluorescently labeled NBD-phospholipid probes as judged by the dithionite quenching assay, see Boon, J. M. & Smith, B. D. (2002) Med. Res. Rev., 22, 251–81, the entire contents and disclosure of which is hereby incorporated by reference.

Erythrocyte Studies with PSS-380

Aliquots (10 μL) containing 4.0×10$^9$ of normal or "scrambled" erythrocytes were added to a solution of PSS-380 (1 μM, 3 mL) in 5 mM TES, 150 mM NaCl, pH 7.4. The erythrocytes were prepared in the following way. Fresh human blood was collected in ice-cold phosphate-buffered-saline (PBS) containing 10 U/mL of heparin. The samples were centrifuged and the supernatant and the top 10% of the erythrocytes were removed. The wash was repeated two more times. An equal volume of PBS was added to the remaining pellet. The desired number of cells was removed, centrifuged and the supernatant discarded. Four volumes of lysis buffer (0.1×PBS containing 0.1 mM EGTA, 1 mM MgCl$_2$, and 1% BSA, plus 1 mM CaCl$_2$ for "scrambled" erythrocytes only) were added to the pellet. The suspensions were vortexed and the lysed cells were placed on ice. After 2 minutes, the cells were resealed by adding 0.4 volumes (relative to the size of the original pellet) of 10×PBS. The tubes were gently inverted and warmed to 37° C. After 30 minutes, 100 volumes of PBS were added, then the cells were centrifuged into pellets, washed three times, and resuspended in TES buffer for use.

Cell Staining and Fluorescence Microscopy with PSS-380

Jurkat E6-1 cells were grown in RPMI 1640 growth media supplemented with 10% fetal bovine serum. MCF-7 cells were grown in DMEM growth media with 10% fetal bovine serum. These adherent cells were grown to 80% confluence directly in 16-well chamber microscope slides. Suspended cells (Jurkat) were grown to a density of 1×10$^6$ cells/mL. Before staining with annexin V-FITC, the growth media was changed to a binding buffer containing 5 mM TES/145 mM NaCl, 2.5 mM CaCl$_2$, at pH 7.4. The cells were incubated with annexin V-FITC (10 µL of Pharmingen stock solution per mL cell suspension), 7AAD (5 µL of 50 µg/mL stock solution per mL cell suspension), and PSS-380 (20 µL of 1 mM stock solution per mL cell suspension) for 15 minutes at 37° C. The incubation mixture was aspirated and changed to a buffer containing 5 mM TES, 145 mM NaCl, pH 7.4. At this point, the Jurkat cell suspensions were added to 16-well chamber-slides. Cells were observed directly on an Axiovert S100 TV microscope (Carl Zeiss) equipped with filter sets DAPI/Hoechst/AMCA, FITC/RS-GFP/Bodipy/Fluo3/DiO, Cy3 (Chroma). Pictures were taken using a black and white digital camera and colored afterwards using Photoshop 6.0 software package (Adobe).

Flow Cytometry with PSS-380

HL60 cells were cultured in RPMI 1640 medium and removed after overnight expansion. Apoptosis was induced by treatment with camptothecin (10 µM) for 6 hours. Before staining, the cells were washed twice (300×g, 10 minutes) in cold Earle's Balanced Salt Solution followed by resuspension in binding buffer to a concentration of ~1×10$^6$ cells/mL. Aliquots (100 µL) of this cell suspension were transferred to 12×75 mm test tubes, along with appropriate amounts of annexin V-FITC (5 µL of Pharmingen stock solution), PSS-380 (10 µL of 1 mM stock solution), and PI (10 µL of 50 µg/mL stock solution). The tubes were gently agitated for 15 minutes at room temperature in the dark, then an additional 400 µL of binding buffer was added. Another incubation for 10 minutes was followed by a wash (300×g, 10 minutes) and resuspension in 400 µL of Earle's Buffer prior to flow cytometry. All tubes were analyzed within 1 hour of preparation. Flow cytometry was performed using a Coulter Altra flow cytometer equipped with an Enterprise II laser. PSS-380 was excited at 350 nm and emission was collected at 440 nm, annexin V was excited at 488 nm with emission at 525 nm, and PI was excited at 488 nm with emission at 617 nm. The cell analysis was gated to only allow counting of PI negative cells.

Results with PSS-380

Figure 1:
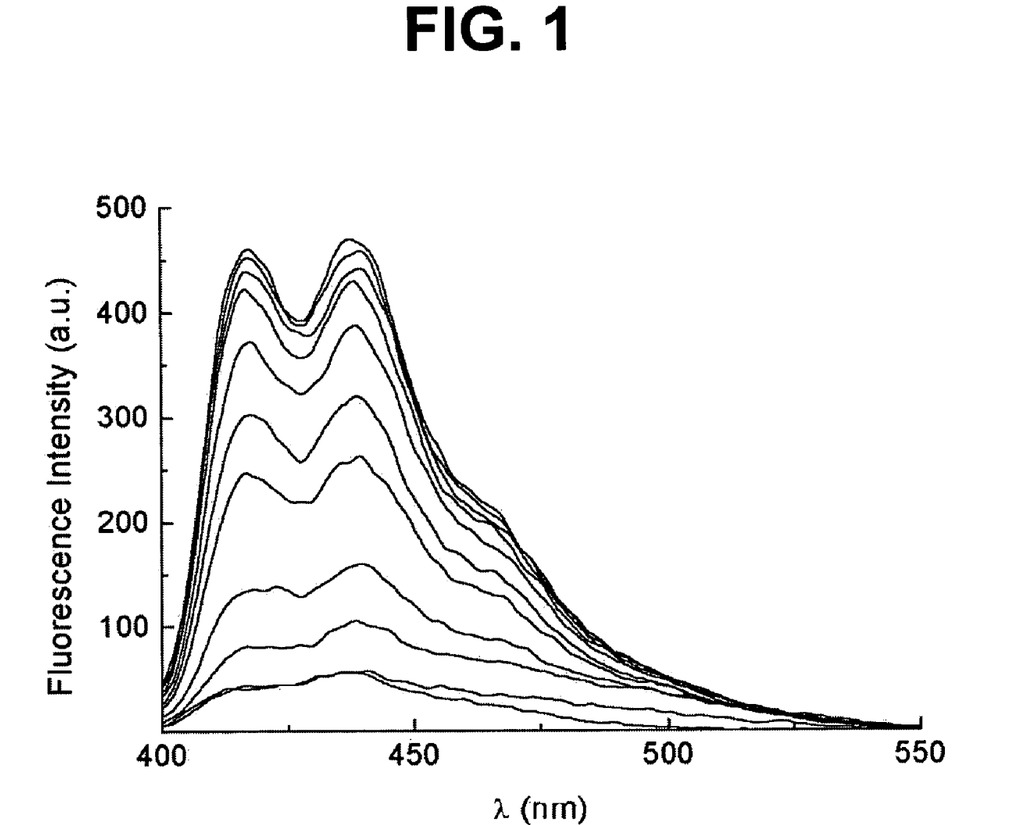
FIG. 1 shows fluorescence emission (ex 380 nm) of PSS-380 (1 µM) in HEPES buffer 10 mM, pH 7.2 upon addition of 1 to 10 µM (total phospholipid concentration) of POPC:POPS (50:50) vesicles.
Figure 2:
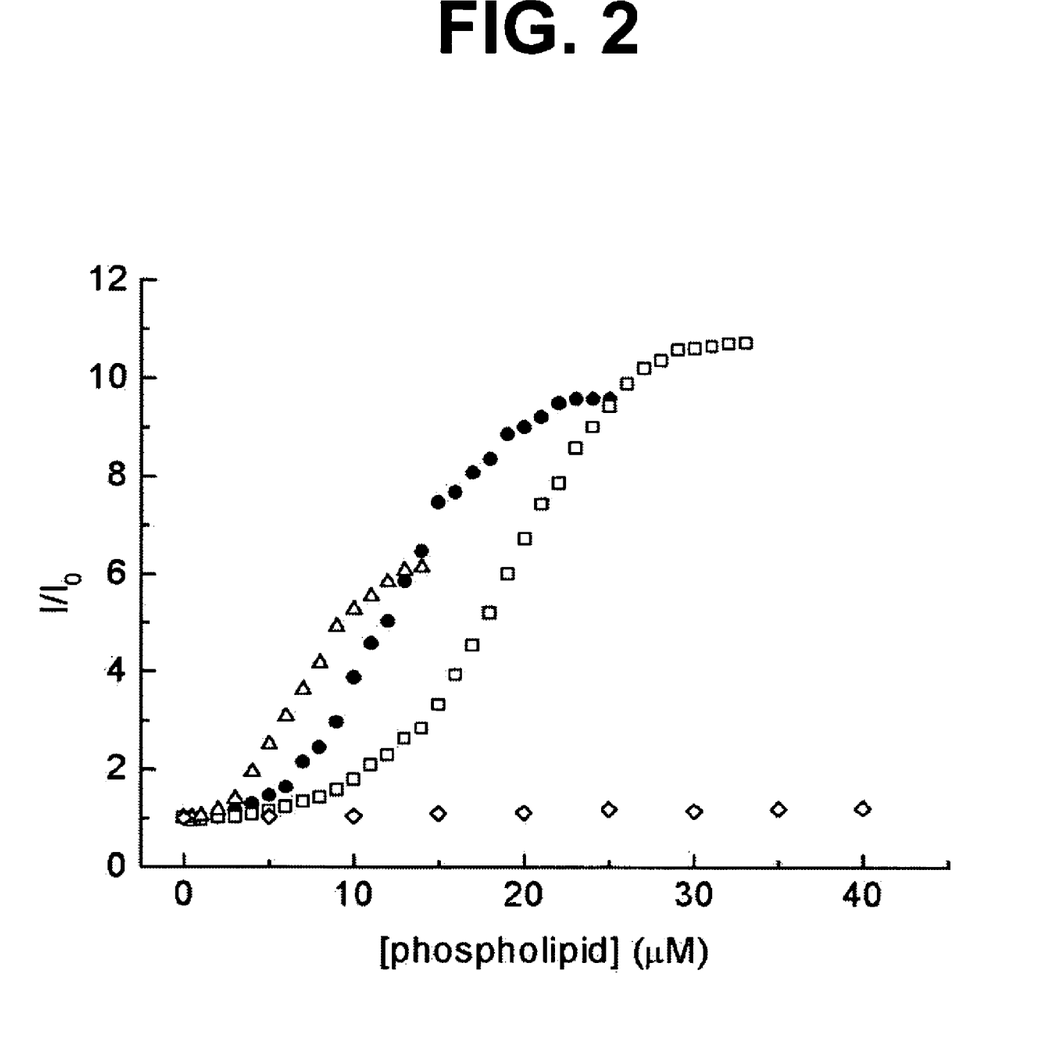
FIG. 2 shows a change in fluorescence intensity $I/I_o$ (ex 380, em 440 nm) of PSS-380 (1 µM) in HEPES buffer (10 mM, pH 7.2) upon addition of 100 nm unilamellar vesicles composed of 100% POPC (diamonds), or 50:50 mixtures of POPC:POPS (filled circles), POPC:POPG (squares), or POPC:POPA (triangles)
Figure 3:
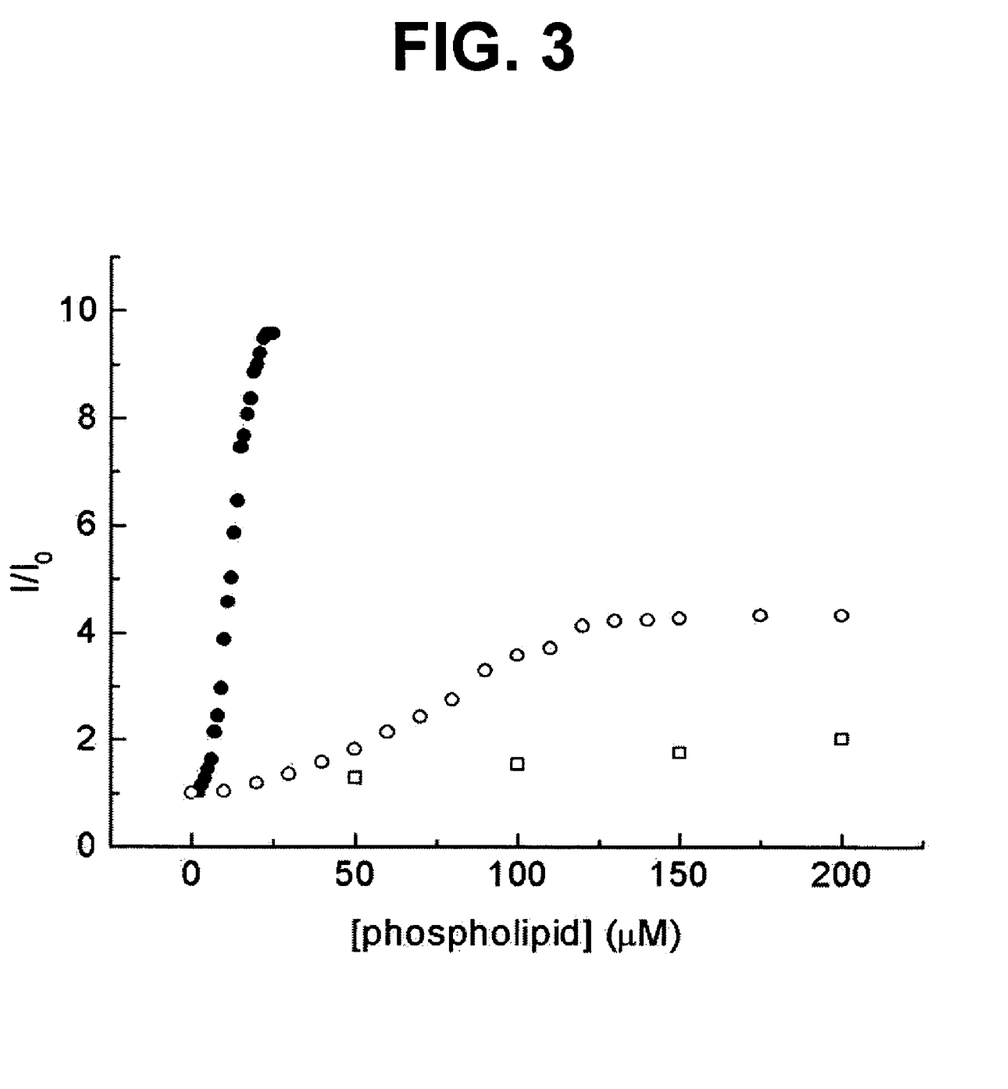
FIG. 3 shows a change in fluorescence intensity $I/I_o$ (ex 380, em 440 nm) of PSS-380 (1 µM) in HEPES buffer (10 mM, pH 7.2) upon addition of 100 nm unilamellar vesicles composed of POPC:POPS 50:50 (filled circles), POPC:POPS 95:5 (open circles), 100% POPC (squares)

The change in fluorescence emission for PSS-380 upon addition of 1-palmitoyl-2-oleoyl-sn-glycero-3-phosphocholine (POPC): 1-palmitoyl-2-oleoyl-sn-glycero-3-phosphoserine (POPS) (50:50) vesicles is shown in FIG. 1. Plots of change in fluorescence intensity upon addition of vesicles composed of 100% POPC, and 50:50 mixtures of POPC: POPS, POPC:1-palmitoyl-2-oleoyl-sn-glycero-3-phosphoglycerol (POPG), and POPC: 1-palmitoyl-2-oleoyl-sn-glycero-3-phosphatidic acid (POPA) are shown in FIG. 2. No change in the fluorescence of PSS-380 was observed after addition of zwitterionic POPC vesicles. However, fluorescence intensity increased if the vesicles contained an anionic phospholipid in the order POPG (eleven-fold increase) >POPS (ten-fold increase)>POPA (six-fold increase). Even vesicles containing 5 mol % of POPS produced a four-fold rise in fluorescence emission (FIG. 3). The titration curves in FIGS. 2 and 3 have sigmoidal shapes which suggest that the sensor binds to the vesicles with positive cooperativity; however, at this point other explanations cannot be ruled out such as increased levels of PSS-380 on the vesicle surface at low phospholipid concentrations producing complexes with decreased fluorescence. For example, the data in FIGS. 2 and 3 may be due to a three-stage binding model; the sensor may be weakly fluorescent in bulk solution, weakly fluorescent as a 2:1 sensor:PS complex on a PS-rich vesicle surface, and highly fluorescent as a 1:1 sensor:PS complex on the vesicle surface. Macroscopically, the sensing effect is cooperative. Not only does membrane affinity increase with raised PS-levels, so does the maximum fluorescence at sensor saturation.

Although the fluorescence emission of PSS-380 increases in the presence of vesicles containing PS, it is unchanged if the PS is monodispersed. For example, dihexanoylphosphatidylcholine (DHPC) and dihexanoylphosphatidylserine (DHPS) are PC and PS analogues with short $C_6$-acyl chains, and therefore do not aggregate at micromolar concentrations. Titration of PSS-380 with increasing amounts of a DHPC:DHPS (1:1) mixture results in no change in fluorescence intensity. Further evidence that PSS-380 has a weak affinity for DHPS and DHPC in water was gained from $^{31}$P NMR titration experiments. The $^{31}$P signals for phospholipid head groups hardly move upon addition of PSS-380. This is in line with previous studies with PSS-380 showing that it has low affinity for neutral or mono-anionic molecules in water, Ojida, A., Mito-Oka, Y., Inoue, M. A. & Hamachi, I. (2002) J. Am. Chem. Soc., 124, 6256–6258, the entire contents and disclosure of which is hereby incorporated by reference.

Figure 4:
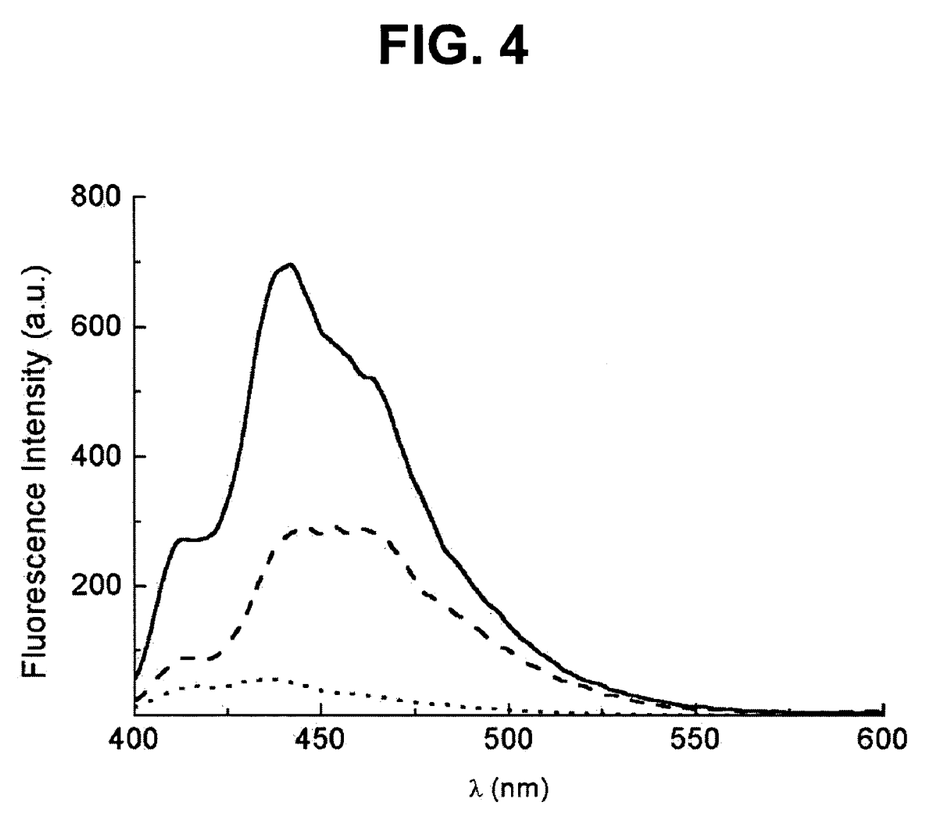
FIG. 4 shows fluorescence emission of PSS-380 (1 µM) in 5 mM TES, 150 mM NaCl, pH 7.4 upon excitation at 380 nm (dotted line), presence of $4 \times 10^9$ normal erythrocytes (dashed line), or same number of symmetrical "scrambled" erythrocytes (solid line)

The present invention also examined the behavior of PSS-380 in cellular systems. First, the ability of PSS-380 to detect the presence of PS on the surface of erythrocytes, a relatively simple cell system that normally maintains most of its PS in the inner monolayer of its plasma membrane, was examined. Using a standard procedure, "scrambled" erythrocytes were prepared with a symmetrical distribution of PS on both sides of the plasma membrane, see Kamp, D., Sieberg, T. & Haest, C. W. (2001) Biochemistry, 40, 9438–46, the entire contents and disclosure of which is hereby incorporated by reference. As shown in FIG. 4, the "scrambled" erythrocytes induce a much higher PSS-380 fluorescence, compared to an equal number of normal erythrocytes, which is attributed to their higher levels of externalized PS.

The ability of PSS-380 to detect cell apoptosis was also examined in the present invention. This was approached in three ways. First, it was assessed whether PSS-380 could be used in a single-well, bulk fluorescence assay for apoptosis. PSS-380 emission was on average found to be twice as intense (±5%) in the presence of apoptotic Jurkat cells (apoptosis induced by the anticancer drug camptothecin) as in the presence of an equal number of live cells. Thus, cell apoptosis may be detected qualitatively using PSS-380 in a simple, single-well, bulk fluorecence assay.

Figure 5:
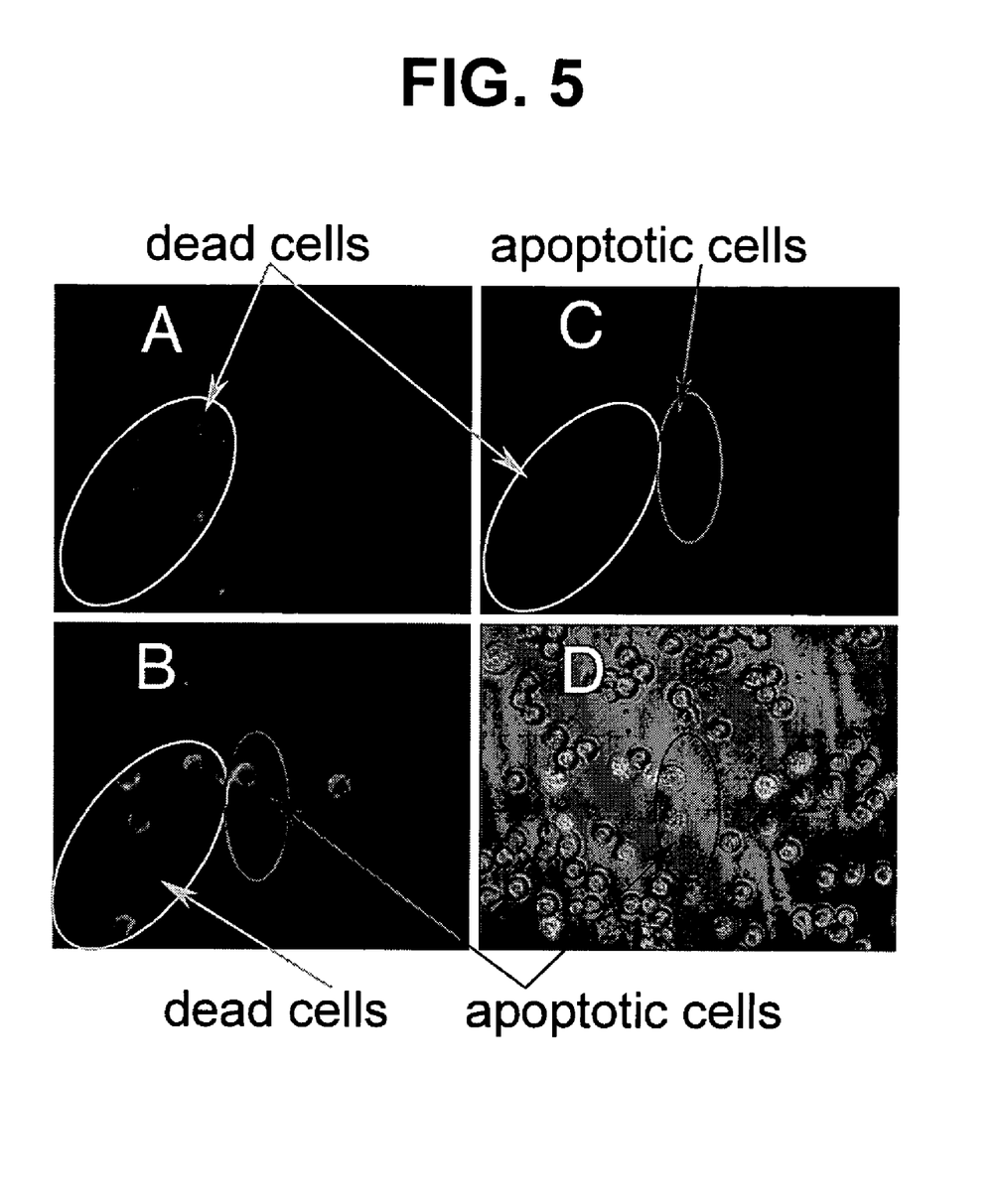
FIG. 5 shows apoptosis of Jurkat cells induced by incubation with calcium ionophore A23187 (0.2 µM) for 30 minutes, with cells stained simultaneously with 7AAD (panel A), annexin V-FITC (panel B), PSS-380 (panel C), and panel D as a merge of (A), (B), (C), and a phase contrast image of the same cells in which live cells are not stained by any of the dyes.
Figure 6:
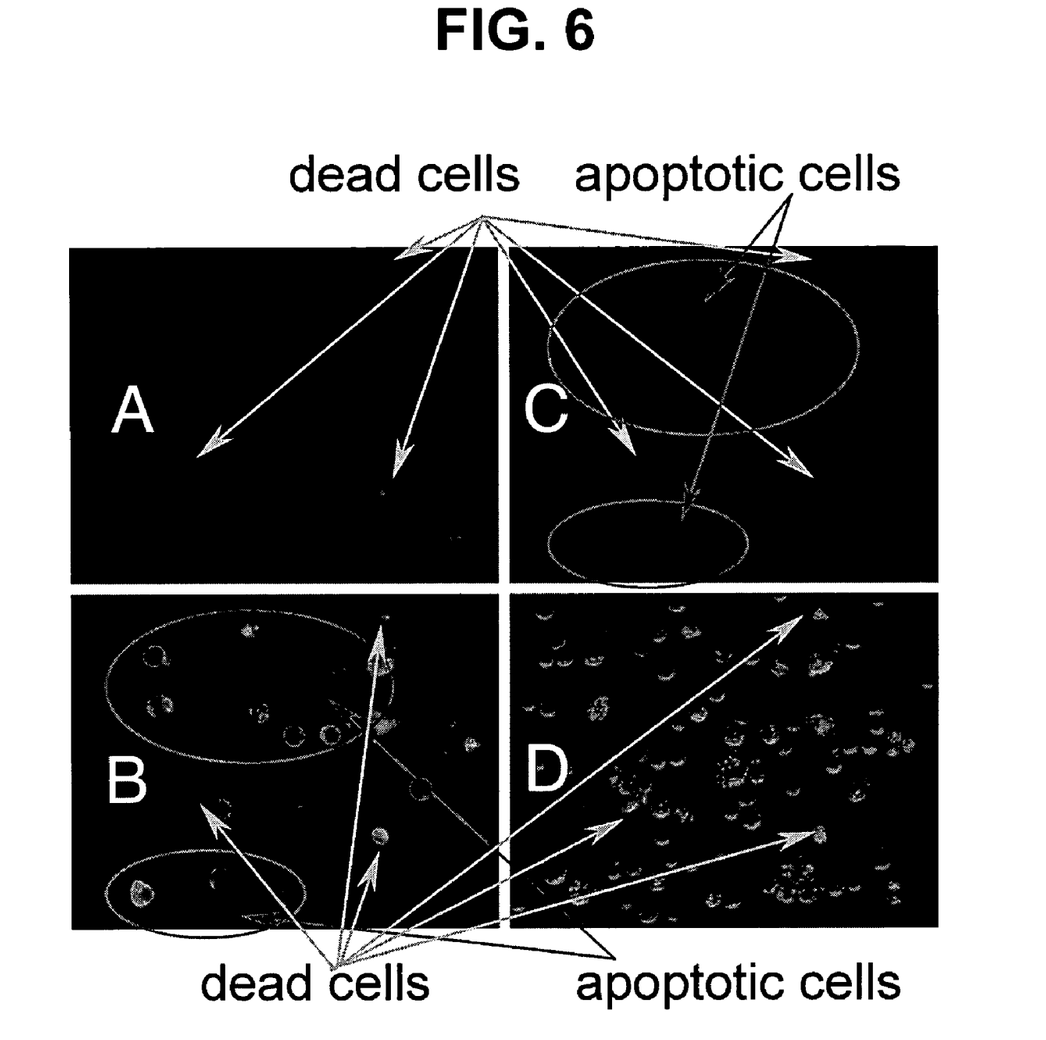
FIG. 6 shows apoptosis of Jurkat cells induced by incubation with camptothecin (10 μM) for 4 hours, with cells stained simultaneously with 7AAD (panel A), annexin V-FITC (panel B), PSS-380 (panel C), and panel D as a merge of (A), (B), (C), and a phase contrast image of the same cells in which live cells are not stained by any of the dyes.
Figure 7:
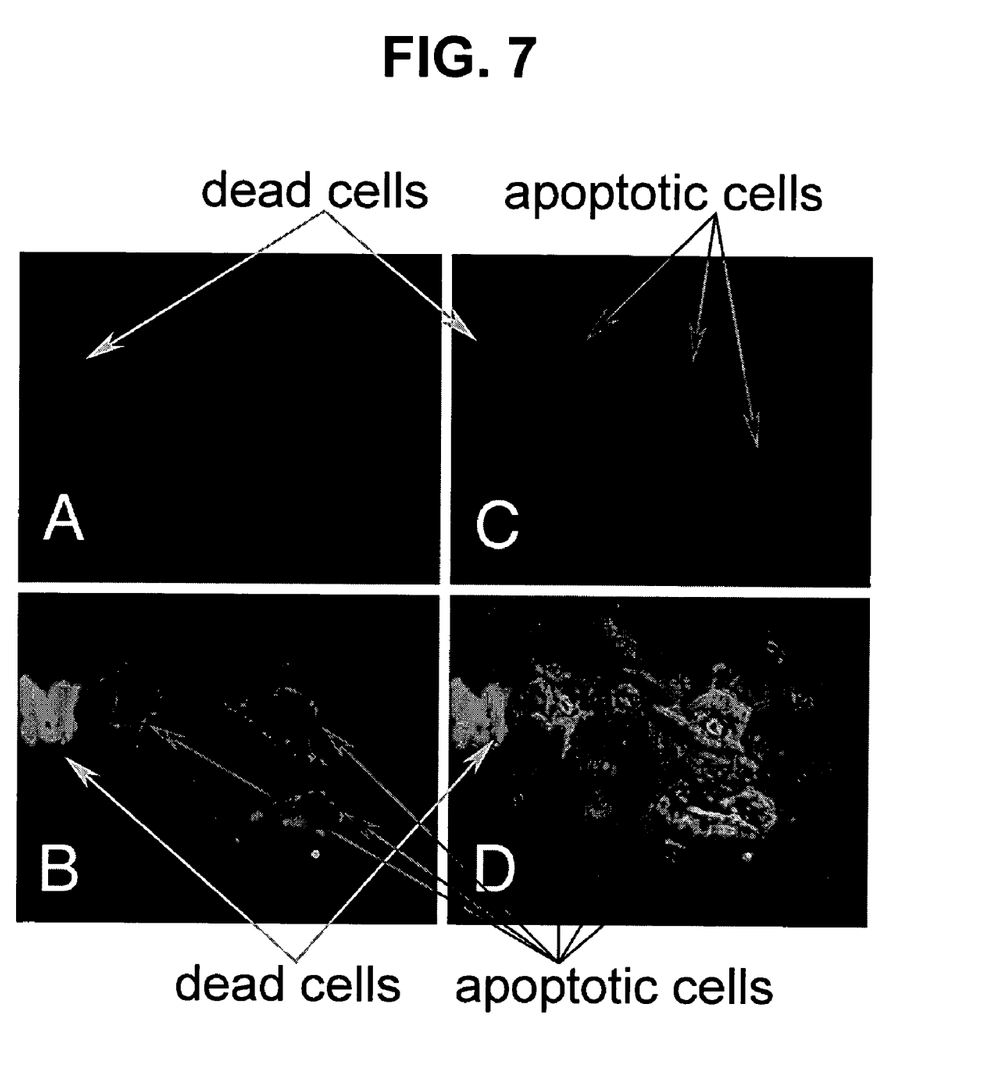
FIG. 7 shows apoptosis of MCF-7 cells induced by incubation with calcium ionophore A23187 (2.5 μM) for 15 minutes with cells stained simultaneously with 7AAD (panel A), annexin V-FITC (panel B), PSS-380 (panel C), and panel D as a merge of (A), (B), (C), and a phase contrast image of the same cells in which live cells are not stained by any of the dyes.

Fluorescence microscopy was also used to evaluate if PSS-380 could identify sub-populations of live, apoptotic, and dead cells. Cell apoptosis was induced by treatment with camptothecin, or the calcium ionophore A23187. The drug-treated cells and untreated control cells were subsequently stained with a mixture of annexin V-FITC (green), PSS-380 (blue) and 7AAD (red). FIGS. 5, 6 and 7 display typical microscopic images produced using this method. Live cells are not stained by any of the dyes; whereas, staining by 7AAD identifies dead cells with permeable membranes. Cells that are only stained by annexin V-FITC or PSS-380 are defined as apoptotic. The microscopic images show a slight statistical variation in cell staining, due in part to the fact that PSS-380 and annexin V-FITC are competing for the same cell surface binding sites. If the staining experiments are repeated using either annexin V or PSS-380 alone, the emission from positive cells is more homogeneous and with similar intensity.

Figure 8:
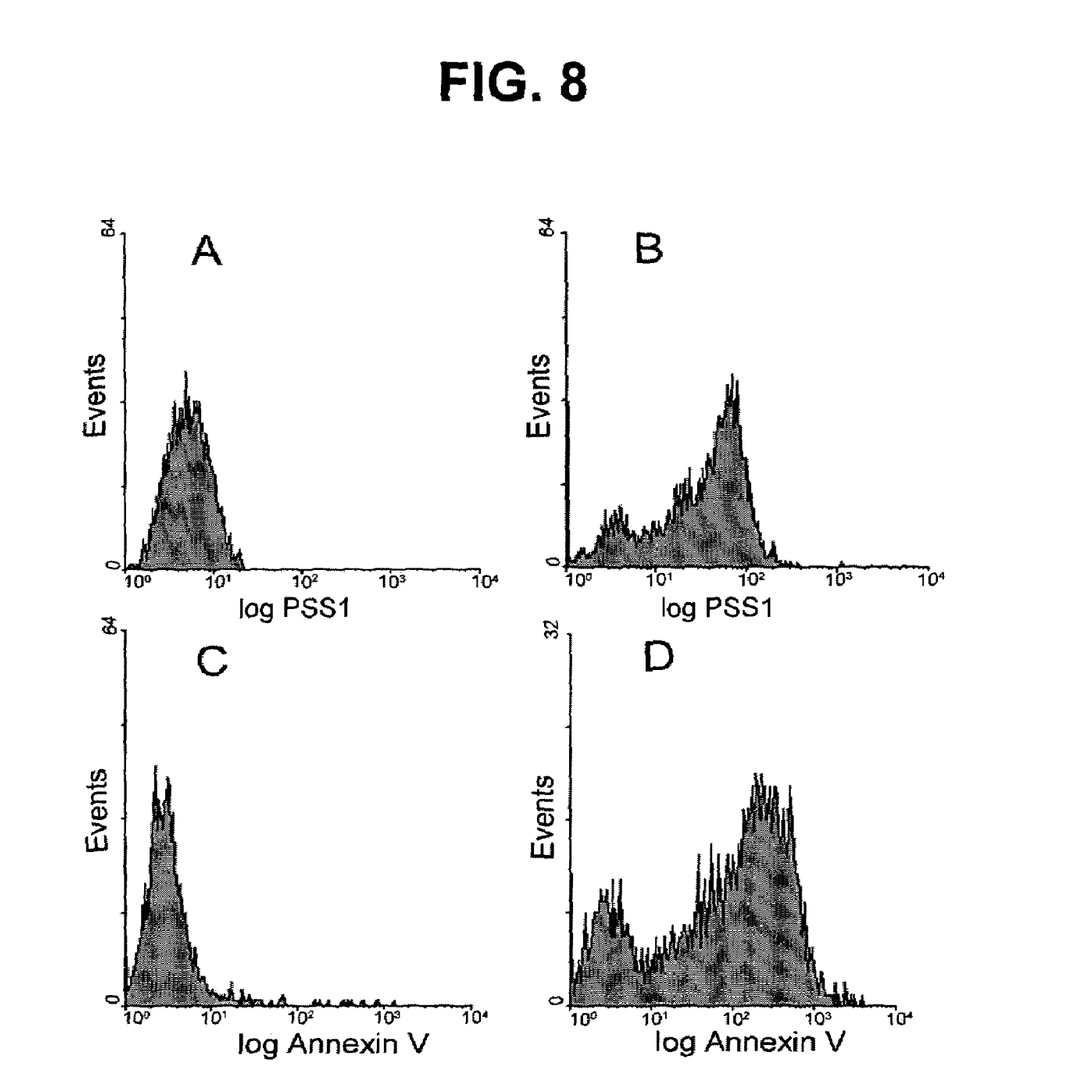
FIG. 8 is a flow cytometry analysis showing that treatment of HL60 cells with camptothecin (10 μM) for 6 hours induces cell apoptosis, in which panels A and C are untreated cells labeled with PSS-380 (ex 350, em 440 nm) and annexin V-FITC (ex 488, em 525 nm), and panels B and D identify the cells that become apoptotic, wherein all data shown are PI negative cells.

The most compelling evidence that PSS-380 and annexin V are detecting the same population of apoptotic cells was gained from flow cytometry analysis of HL60 cells that were treated with camptothecin. The two sets of data in FIG. 8 (UV excitation of PSS-380 and visible excitation of annexin V-FITC) lead to the same conclusion, that 80–85% of the viable cells (identified because they are not stained by the vital cell dye PI) are apoptotic.

PSS-380 binding to apoptotic cells is almost instantaneous, and is not noticeably inhibited by the presence of $Ca^{2+}$. Furthermore, PSS-380 staining fades rapidly when the mixture is treated with 10 mM EDTA, confirming the critical role of the zinc atoms for cell binding, and also showing that PSS-380 is not internalized by the cells. Tests were performed to establish the toxicity of PSS-380. Flow cytometry showed that exposure of Jurkat cells to 100 μM of PSS-380 for one hour produced no change in cell viability, as judged by the lack of staining by PI.

The flow cytometry data indicates that PSS-380 and annexin V are binding to the same population of apoptotic cells. The microscopy data indicates that PSS-380 staining is more intense than annexin V, which may be attributed to annexin V's much larger size per fluorophor. It has been estimated that annexin V (molecular weight of 35 kD) covers a surface binding area of about 50 phospholipid molecules, Meers, P., Daleke, D., Hong, K. & Papahadjopoulos, D. (1991) Biochemistry, 30, 2903–2908, the entire contents and disclosure of which is hereby incorporated by reference. Thus, it is possible that more than ten PSS-380 molecules (molecular weight of 1 kD) may bind to the same membrane area as one annexin V molecule.

There is a range of methods for apoptosis detection and each has advantages and disadvantages. For example, there are assays that monitor changes in cell morphology, changes in the biochemistry of the cell cytoplasm, and DNA fragmentation, see van Heerde, W. L., Robert-Offerman, S., Dumont, E., Hofstra, L., Doevendans, P. A., Smits, J. F., Daemen, M. J. & Reutelingsperger, C. P. (2000) Cardiovasc. Res., 45, 549–59, and Kimura, E.; Aoki, S.; Kikuta, E.; Koike, T. (2003) Proc. Natl. Acad. Sci., USA 100, 3731–3736, the entire contents and disclosures of which are hereby incorporated by reference. An important limitation with these techniques is that they measure parameters of the late execution phase of apoptosis, at which point valuable information may be lost. On the other hand, the appearance of cell surface PS is a global indicator of the intermediate stages of apoptosis, and this early detection point is one of the major advantages of the annexin V assay. However, the PS/annexin V binding process is slow and $Ca^{2+}$ dependent, which limits its utility in kinetic assays. The microscopy and flow cytometry data for PSS-380 indicate that the synthetic sensor PSS-380 provides the same apoptosis detection information as annexin V, but it is easier to handle and store. Not only should PSS-380 be useful as an apoptosis sensor in cell biology research, it may also have utility in high-throughput assays for drug discovery, as well as automated monitoring of animal cell culture technology, see Plasier, B., Lloyd, D. R., Paul, G. C., Thomas, C. R. & Al-Rubeai, M. (1999) J. Immunol. Meth., 229, 81–95, the entire contents and disclosures of which are hereby incorporated by reference.

PSS-380 may be used immediately by biomedical researchers as a chemical substitute for fluorescently labelled annexin V protein. PSS-380 allows detection of apoptotic cells using a fluorescent microscope. It may also be used in flow cytometers that are equipped with a UV laser.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for determining the presence of monoanionic phospholipids in a sample of cells or vesicles, comprising:
    introducing a low molecular weight compound having the following structure to said sample, wherein said low molecular weight compound binds to said monoanionic phospholipids of said cells or vesicles; and detecting the presence of monoanionic phospholipids by fluorescence emission from said low molecular weight compound wherein A is a weakly coordinating counter anion and n indicates the stoichiometry.

2. The method of claim 1, wherein said monoanionic phospholipids comprise phosphatidylserine.

3. The method of claim 1, wherein said method is carried out in a low calcium environment.

4. The method of claim 1, wherein said method is carried out in a substantially calcium free environment.

5. The method of claim 1, wherein binding of said low-molecular weight compound to said monoanionic phospholipid is independent of calcium concentration.

* * * * *